United States Patent [19]

Lingenfelter

[11] Patent Number: 4,668,867
[45] Date of Patent: May 26, 1987

[54] RADIATION GAUGE FOR DETERMINING WEIGHT PERCENTAGES OF THE CONSTITUENTS OF GRAPHITE-EPOXY COMPOSITE MATERIALS

[75] Inventor: Dean E. Lingenfelter, Fair Oaks, Calif.

[73] Assignee: Lockheed Missiles & Space Company, Inc., Sunnyvale, Calif.

[21] Appl. No.: 737,987

[22] Filed: May 28, 1985

[51] Int. Cl.$^4$ .............................................. G01N 23/08
[52] U.S. Cl. ................................ 250/358.1; 250/393; 250/394; 250/395; 378/53
[58] Field of Search ............... 378/53; 250/358.1, 395, 250/394, 393, 363 R, 367, 341, 339

[56] References Cited

U.S. PATENT DOCUMENTS 3,082,323  3/1963  Chope et al. ..................... 250/308
3,655,964  4/1972  Slight ............................... 378/53
4,363,968  12/1982  McGowan et al. ................ 250/339
4,577,337  3/1986  Light ................................ 378/44

Primary Examiner—Janice A. Howell
Assistant Examiner—Constantine Hannaher
Attorney, Agent, or Firm—John J. Morrissey

[57] ABSTRACT

A sample 10 of a composite material, such as a graphite-epoxy composite, is exposed to radiation in three distinct energy bands emanating from sources 12, 13 and 14, respectively. Corresponding detectors 16, 17 and 18 are positioned to measure the amount of energy in each band transmitted through the sample. Weight percentages of three different constituents of the sample 10 are calculated from a relatively simple algorithm whose variables include a ratio for each of said energy bands of the amount of energy that would be detected if the sample were not present in the radiation to the amount of energy transmitted through the sample when the sample is exposed to the radiation.

21 Claims, 1 Drawing Figure

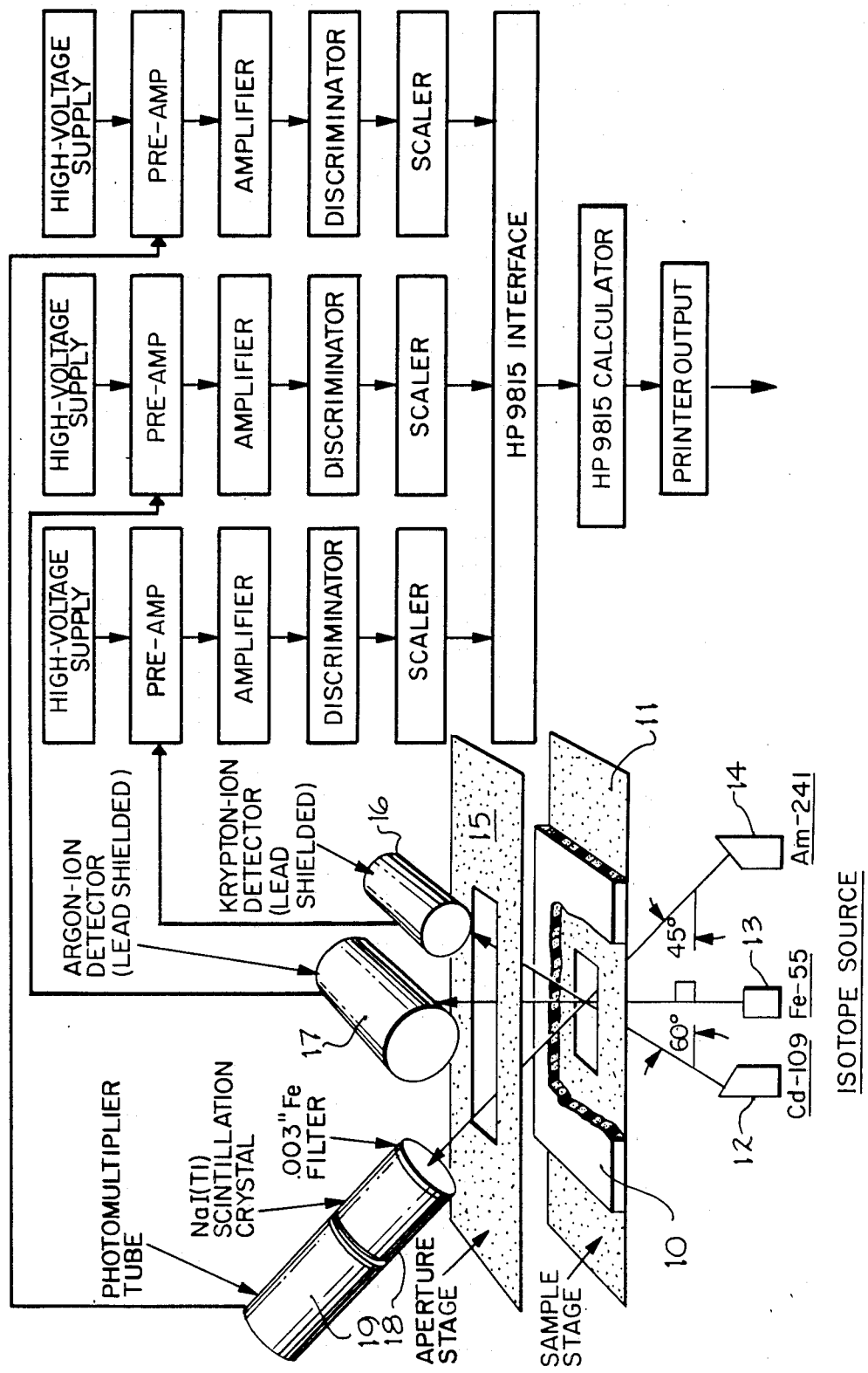

RADIATION GAUGE FOR DETERMINING WEIGHT PERCENTAGES OF THE CONSTITUENTS OF GRAPHITE-EPOXY COMPOSITE MATERIALS

TECHNICAL FIELD

This invention relates to radiation gauge techniques for measuring weight percentages of the constituents of composite materials.

The Government has rights in this invention pursuant to Contract N00030-74-C-0100 awarded by the Department of the Navy.

BACKGROUND

Radiation gauge techniques have been used in the prior art to measure weight percentages, or parameters related to weight percentages (e.g., fiber volume), for the constituents of certain kinds of composite materials such as fiberglass-epoxy composites. Technical Report AFML-TR-68-233 entitled "Development of Nondestructive Tests for Predicting Elastic Properties and Component Volume Fractions in Reinforced Plastic Composite Materials", published by the Air Force Materials Laboratory, Air Force Systems Command, Wright-Patterson Air Force Base, Ohio in February 1969, describes radiation gauge techniques that have been used for non-destructively determining weight percentages of the constituents of composite materials.

In general, accurate measurements for weight percentages of the constituents of a composite material have been obtainable in the prior art only in cases where the constituents of the composite material have different atomic numbers, and where the radiation absorption coefficients of the constituents are significantly different from each other for at least one wavelength. For composite materials such as graphite-epoxy composites, the radiation gauge techniques developed in the prior art have generally been unable to provide accurate measurements for constituent weight percentages and for fiber volume.

A graphite-epoxy composite essentially comprises graphite fibers (pure carbon) and an epoxy resin, which are mixed in specified proportions according to the particular application. Epoxy resin is typically composed of carbon (approximately 70 percent by weight) and varying quantities of other elements such as hydrogen, nitrogen and oxygen. From the standpoint of distinguishing quantitatively between the carbon fibers and the epoxy resin in a graphite-epoxy composite, the epoxy resin can be characterized as an impure carbon, i.e., carbon with an admixture (typically 30 percent by weight) of other elements. Unfortunately for radiation gauge measurement techniques of the prior art, the presence of the other (i.e., non-carbon) elements in the epoxy resin typically does not sufficiently change the value of the effective radiation absorption coefficient of the epoxy resin (i.e., impure carbon) from the value of the radiation absorption coefficient of the carbon fibers (i.e., pure carbon).

Graphite-epoxy composites, which are currently attracting attention for use in, e.g., aircraft and space vehicle structures, provide examples of particular kinds of composite materials for which radiation gauge techniques of the prior art were ineffective in measuring constituent weight percentages and related parameters. If the epoxy resin in a graphite-epoxy composite is considered as a single constituent (viz., impure carbon), the effective radiation absorption coefficient of the epoxy resin is not sufficiently different from the radiation absorption coefficient of pure carbon to enable radiation gauge techniques known in the prior art to distinguish unambiguously between the epoxy resin and the pure carbon.

In practice, the measurement of graphite fiber content by weight percentage or by volume in graphite-epoxy composites has heretofore been accomplished by destructive testing methods. A preferred destructure testing method for making such measurements was described in Technical Publication ASTM D3171 published by the American Society for Testing and Materials in the "Annual Book of ASTM Standards", Part 36, (1984).

SUMMARY OF THE INVENTION

It is an object of the present invention to provide a non-destructive method whereby accurate weight percentage measurements of the constituents of a composite material can be obtained, regardless of the values of the radiation absorption coefficients of the individual constituents of the composite material. Weight percentage measurements made according to the present invention can be converted to volume percentage measurements by a simple mathematical algorithm.

It is also an object of the present invention to provide a non-destructive method for measuring ply-count in a composite material comprising fibrous constituents.

It is likewise an object of the present invention to provide a radiation gauge that can be used for non-destructively measuring relative percentages by weight of the constituents of composite materials, particularly composite materials for which the radiation absorption coefficients and/or the atomic numbers of the constituents are very close in value.

In accordance with the method of the present invention, a sample of a composite material is exposed to radiation emanating from a plurality of different sources, the radiation from each source having a characteristic narrow energy band. Ordinarily, the radiation sources used in a radiation gauge according to the present invention are radioactive isotopes. A corresponding number of detectors, which may be conventional radiation detector devices, are positioned to measure the amount of energy in each energy band transmitted through the sample of composite material. Each detector is most sensitive to a particular one of the transmitted energy bands, and measures the absorption characteristics of the composite material for that particular energy band.

The amount N of energy in a particular narrow energy band transmitted through the sample of composite material (as measured by the detector sensitive to that particular energy band) is given by the radiation absorption equation $$N = N_0 e^{-\mu t}, \tag{1}$$

where $N_0$ is the amount of energy from the radiation source emitting that particular energy band that the detector would measure in the absence of the sample of composite material, t is the thickness of the sample of composite material, and $\mu$ is the effective radiation linear absorption coefficient of the composite material for the particular energy band.

The effective radiation linear absorption coefficient $\mu$ for the composite material is the weighted average of the individual radiation absorption coefficients for the constituents comprising the composite material. Thus, for a sample of graphite-epoxy composite having graphite fibers as a first constituent and epoxy resin as a second constituent, the effective radiation linear absorption coefficient $\mu$ is given by $\mu = \alpha_1\mu_1 + \alpha_2\mu_2$, wherein $\mu_1$ is the radiation absorption coefficient of the graphite fibers (i.e., pure carbon) and $\mu_2$ is the radiation absorption coefficient of the epoxy resin (i.e., impure carbon), and where $\alpha_1$ and $\alpha_2$ are the fractional weight percentages of the graphite fibers and the epoxy resin, respectively.

In general, the amount of energy in a given narrow energy band absorbed by a material depends upon the energy level of the radiation, and upon the electron density and the volume density of the material through which the radiation is being transmitted. The volume density $\rho$ of each constituent in a composite material can usually be determined quite precisely by conventional analytical methods. It is, therefore, convenient to write the radiation absorption equation for a given material in the form $N = N_0 e^{-(\mu/\rho)\rho t}$, where $\rho$ has a known value for the particular material, and where the quantity $(\mu/\rho)$ is independent of volume density. The quantity $(\mu/\rho)$ is called the mass absorption coefficient, or the mass absorption cross section.

In terms of the individual constituents of a two-constituent composite material, the radiation absorption equation can be written in the form $$N = N_0 e^{-[(\mu/\rho)_1 \alpha_1 \rho_1 + (\mu/\rho)_2 \alpha_2 \rho_2]t}, \quad (2)$$

where $\rho_1$ and $\rho_2$ are the volume densities, $\alpha_1$ and $\alpha_2$ are the fractional weight percentages, and $(\mu/\rho)_1$ and $(\mu/\rho)_2$ are the mass absorption cross sections of the first and second constituents, respectively, of the two-constituent material. The mass absorption cross sections $(\mu/\rho)_1$ and $(\mu/\rho)_2$ are dependent on the energy level of the radiation to which the composite material is exposed. Thus, the relative weight percentages of the first and second constituents of the composite material can be determined by solving equation (2) for $\alpha_1$ and $\alpha_2$ for two different energy levels.

For a given energy level $E_1$, $$\ln(N_0/N)_{E_1} = [(\mu/\rho)_{11}\alpha_1\rho_1 + (\mu/\rho)_{21}\alpha_2\rho_2]t. \quad (3)$$

Similarly, for another energy level $E_2$, $$\ln(N_0/N)_{E_2} = [(\mu/\rho)_{12}\alpha_1\rho_1 + (\mu/\rho)_{22}\alpha_2\rho_2]t. \quad (4)$$

Solving equations (2) and (3) simultaneously for $\alpha_1$ and $\alpha_2$ in matrix form yields:

$$\alpha_1 = \frac{\frac{1}{\rho_1 t}\begin{vmatrix}\ln(N_0/N)_{E_1} & (\mu/\rho)_{21} \\ \ln(N_0/N)_{E_2} & (\mu/\rho)_{22}\end{vmatrix}}{\begin{vmatrix}(\mu/\rho)_{11} & (\mu/\rho)_{21} \\ (\mu/\rho)_{12} & (\mu/\rho)_{22}\end{vmatrix}} \quad (5)$$

and $$\alpha_2 = \frac{\frac{1}{\rho_2 t}\begin{vmatrix}(\mu/\rho)_{11} & \ln(N_0/N)_{E_1} \\ (\mu/\rho)_{12} & \ln(N_0/N)_{E_2}\end{vmatrix}}{\begin{vmatrix}(\mu/\rho)_{11} & (\mu/\rho)_{21} \\ (\mu/\rho)_{11} & (\mu/\rho)_{21}\end{vmatrix}}. \quad (6)$$

The solution algorithms for equations (5) and (6) can take various forms, depending upon the method used to calibrate the detectors measuring the transmitted radiation. However, regardless of the form of the solution algorithms for equations (5) and (6), the quantities $\ln(N_0,N)_{E_1}$, $\ln(N_0/N)_{E_2}$, $(\mu/\rho)_{11}$, $(\mu/\rho)_{21}$, $(\mu/\rho)_{22}$, $\rho_1$, $\rho_2$ and $t$ must be known or computed.

The transmitted energy amounts $N_0$ and $N$ in equations (5) and (6) are readily determinable by measurement. The volume densities $\rho_1$ and $\rho_2$ are known from handbook data or from conventional analytic methods. The various mass absorption cross sections can be determined from handbook data or empirically from control specimens. For a composite-material sample having a thickness $t$ greater than 0.150 inch (about 0.38 cm), the value of $t$ can be directly measured by conventional techniques without introducing significant error. For a composite-material sample having a thickness $t$ less than 0.150 inch (about 0.38 cm), the accuracy with which the value of $t$ can be directly measured might not be sufficient, and therefore it is expedient to combine $t$ with $\rho$ to create a parameter $\rho t$ called "areal mass" (whose units are $g/cm^2$). The value of the areal mass $\rho t$ determined empirically from mass and area measurements of the sample. Thus, the fractional weight percentages $\alpha_1$ and $\alpha_2$ of the constituents of a two-constituent composite material can be measured by exposing a sample of the composite material simultaneously to radiation at two different energy levels $E_1$ and $E_2$.

Since the size of a matrix determinant for a system of equations depends upon the number of separable variables in the system, if an n-constituent composite material is exposed to n different energy levels, $E_1, E_2, \ldots, E_n$, the values of the fractional weight percentages $\alpha_1, \alpha_2, \ldots, \alpha_n$ for the n different constituents would be given by matrix equations with an n-by-n determinant. For thermosetting graphite-eoxy composites, the constituents of the epoxy resin can vary significantly in their individual radiation absorption coefficients. For such a composite, a system of two matrix equations would not permit an accurate characterization of the epoxy resin, and additional equations and energy levels would be needed. In general, a system of n matrix equations using n different radiation energy levels would be necessary for determining the fractional weight percentages of the n different constituents of a composite material that requires the specification of n different constituents for its accurate characterization.

For a thermosetting graphite-epoxy composite, the specification of three constituents would typically be sufficient to provide accurate characterization of the composite, i.e., $(\mu/\rho)_1$ for the carbon fiber, $(\mu/\rho)_2$ for the "impure carbon" constituent of the resin, and $(\mu/\rho)_3$ for a constituent (viz., sulfur) in the resin that cannot be represented by the mass absorption cross section for the "impure carbon" constituent. Thus, for a typical thermosetting graphite-epoxy composite, radiation at three different energy levels $E_1$, $E_2$ and $E_3$ is used, and the values of the fractional weight percentages $\alpha_1$, ahd 2, and $\alpha_3$ are given by the matrix equations:

$$\alpha_1 = \frac{\frac{1}{\rho_{1'}} \begin{vmatrix} \ln(N_0/N)_{E1} & (\mu/\rho)_{21} & (\mu/\rho)_{31} \\ \ln(N_0/N)_{E2} & (\mu/\rho)_{22} & (\mu/\rho)_{32} \\ \ln(N_0/N)_{E3} & (\mu/\rho)_{23} & (\mu/\rho)_{33} \end{vmatrix}}{\begin{vmatrix} (\mu/\rho)_{11} & (\mu/\rho)_{21} & (\mu/\rho)_{31} \\ (\mu/\rho)_{12} & (\mu/\rho)_{22} & (\mu/\rho)_{32} \\ (\mu/\rho)_{13} & (\mu/\rho)_{23} & (\mu/\rho)_{33} \end{vmatrix}}, \quad (7)$$

$$\alpha_2 = \frac{\frac{1}{\rho_{2'}} \begin{vmatrix} (\mu/\rho)_{11} & \ln(N_0/N)_{E1} & (\mu/\rho)_{31} \\ (\mu/\rho)_{12} & \ln(N_0/N)_{E2} & (\mu/\rho)_{32} \\ (\mu/\rho)_{13} & \ln(N_0/N)_{E3} & (\mu/\rho)_{33} \end{vmatrix}}{\begin{vmatrix} (\mu/\rho)_{11} & (\mu/\rho)_{21} & (\mu/\rho)_{31} \\ (\mu/\rho)_{12} & (\mu/\rho)_{22} & (\mu/\rho)_{32} \\ (\mu/\rho)_{13} & (\mu/\rho)_{23} & (\mu/\rho)_{33} \end{vmatrix}}, \quad (8)$$

and $$\alpha_3 = \frac{\frac{1}{\rho_{3'}} \begin{vmatrix} (\mu/\rho)_{11} & (\mu/\rho)_{21} & \ln(N_0/N)_{E1} \\ (\mu/\rho)_{12} & (\mu/\rho)_{22} & \ln(N_0/N)_{E2} \\ (\mu/\rho)_{13} & (\mu/\rho)_{23} & \ln(N_0/N)_{E3} \end{vmatrix}}{\begin{vmatrix} (\mu/\rho)_{11} & (\mu/\rho)_{21} & (\mu/\rho)_{31} \\ (\mu/\rho)_{12} & (\mu/\rho)_{22} & (\mu/\rho)_{32} \\ (\mu/\rho)_{13} & (\mu/\rho)_{23} & (\mu/\rho)_{33} \end{vmatrix}}. \quad (9)$$

The technique described above enables the fractional weight percentages $\alpha_1$, $\alpha_2$ and $\alpha_3$ for a three-constituent composite material to be determined, where one of the constituents of the composite material (e.g., the epoxy resin constituent in the case of a graphite-epoxy composite) includes an element (e.g., sulfur) whose fractional weight percentage varies from one sample to another and whose mass absorption cross section differs significantly from the effective mass absorption cross section of the other elements of that constituent.

For a radiation gauge that operates by exposing a sample of a two-constituent composite to radiation at two different energy levels $E_1$ and $E_2$, the limiting condition for the gauge to be capable of measuring weight percentages of the constituents of the composite is that the determinant $$D = \begin{vmatrix} (\mu/\rho)_{11} & (\mu/\rho)_{21} \\ (\mu/\rho)_{12} & (\mu/\rho)_{22} \end{vmatrix} \quad (10)$$

in equations (5) and (6) be non-zero. Values of the mass absorption cross sections for which $D \gg 1$ result in a system of equations that is relatively insensitive to stability and counting errors. Values of the mass absorption cross sections for which the $D \ll 1$, on the other hand, may result in a system of equations that is incapable of providing physically meaningful results because of overwhelming error propagation. Thus, the radiation sources for such a gauge are selected so that the energy levels $E_1$ and $E_2$ results in a maximum value for D.

For a radiation gauge that operates by exposing a sample of a two constituent composite to radiation at three different energy levels $E_1$, $E_2$ and $E_3$, the limiting condition for the gauge to be capable of measuring weight percentages of the constituents of the composite is that the determinant $$D = \begin{vmatrix} (\mu/\rho)_{11} & (\mu/\rho)_{21} & (\mu/\rho)_{31} \\ (\mu/\rho)_{12} & (\mu/\rho)_{22} & (\mu/\rho)_{32} \\ (\mu/\rho)_{13} & (\mu/\rho)_{23} & (\mu/\rho)_{33} \end{vmatrix} \quad (11)$$

in equations (7), (8), and (9) be non-zero. Thus, the radiation sources for such a gauge are selected so that the energy levels $E_1$, $E_2$ and $E_3$ result in a maximum value for D.

Calibration of the detectors sensitive to the particular energy levels $E_n$ of the radiation sources used in the radiation gauge (where $n=1$, 2 when two radiation sources are used, and where $n=1, 2, 3$ when three radiation sources are used) could be adjusted, if required, for scattered radiation at low energies. For example, at the relatively low 6 keV energy level, the mass absorption cross sections $(\mu/\rho)_1$, and $(\mu/\rho)_2$ for the respective constituents of a two-constituent composite material might have a partial thickness dependence due to scattered radiation redirected toward the detectors.

Where the sample of composite material is a sheet of a graphite epoxy composite for which weight percentages of the graphite fiber constituent and the epoxy resin constituent are to be determined, the chemical formulations and densities of the graphite fibers and of the epoxy resin are generally available in published handbooks. Likewise, the mass absorption cross sections for various energy levels for the elements contained in the graphite fibers and in the epoxy resin are available in published handbooks. See, e.g., CRC Handbook of Chemistry and Physics, published by Chemical Rubber Company, (1971), pages E141-2. These published values permit a theoretical calculation of the mass absorption cross sections for the carbon fiber and the epoxy resin to be made, and therefore permit the value of the determinant D in equations (5) and (6), or in equations (7), (8) and (9), to be determined. This provides a measure of feasibility for the particular energy levels chosen.

For an actual operating system, the mass absorption cross sections of the constituents of the composite material must be determined empirically to account for scatter and noise. In a precise mathematical analysis, significant variations between samples with regard to chemical formulation and/or density are treated as additional variables requiring additional energy levels and additional matrix terms in the equations for the fractional weight percentages $\alpha_1, \alpha_2, \ldots, \alpha_n$.

DESCRIPTION OF THE DRAWING

The drawing is a schematic representation of a radiation gauge according to the present invention utilizing gamma radiation from three different sources for determining weight percentages of the constituents of a composite material.

BEST MODE OF CARRYING OUT THE INVENTION

A radiation gauge according to the present invention is a radiometric gauge, which is well-suited for measuring weight percentages of the constituents of a multiple-constituent composite material (e.g., a graphite-epoxy composite) for which the linear absorption coefficients of the constituents are close in value. A tri-energy radiometric gauge according to a preferred embodiment of the present invention is particularly useful in determining the percentage of graphite fiber by weight in a thermosetting graphite-epoxy composite.

As illustrated schematically in the drawing, a sample 10 of a graphite-epoxy composite, whose graphite fiber concentration by weight is to be measured, is positioned in an apertured lead shield 11. Three different radioactive isotopes 12, 13 and 14, each emitting gamma radiation in an energy band that is characteristic of the particular isotope, are positioned on the other side of the shield 11 so that gamma radiation emissions from the three isotopes are incident upon the same small area (ideally, the same point) on the sample 10. Another apertured lead shield 15 is positioned over the sample 10 to permit radiation transmitted through the sample 10 to pass to appropriately positioned detectors 16, 17 and 18.

In the preferred embodiment, the radioactive isotopes 12, 13 and 14 are cadmium-109 (Cd-109), iron-55 (Fe-55) and americium-241 (Am-241), respectively. These particular isotopes are used because of their well-defined spectra, and because of their locations on the absorption spectrum for the typical constituents of graphite-epoxy composites.

The detectors 16 and 17, which are standard ionization chamber devices, are positioned to receive gamma radiation transmitted through the sample 10 from the isotopes 12 and 13, respectively. The detector 16 is krypton-filled, and the detector 17 is argon-filled. The detector 18 is a sodium iodide (NaI) scintillation detector with a thin NaI crystal that is thallium doped. A photomultiplier tube 19 used to amplify scintillations produced in the NaI crystal.

The electronic circuitry illustrated in the drawing includes three conventional single-channel analyzers, each of which is connected to a corresponding one of the detectors 16, 17 and 18. The three analyzers are all interfaced (as by a Hewlett-Packard 9815 interface) to a calculator (e.g., a Hewlett-Packard 9815 calculator). Count data from the detectors 16, 17, and 18 can be converted by straight-forward algorithms to fractional weight percentages $\alpha_1$, $\alpha_2$ and $\alpha_3$ as discussed above in connection with equations (7), (8) and (9).

In other embodiments using other isotopes, two or more different energy levels could be provided by the same source, provided that the different energy levels are sufficiently resolvable to produce good counting statistics and do not reside in a linear regime of the absorption spectrum of the sample 10. In one such an alternative embodiment, the isotopes 12 and 14 could be Cd-109 and Am-241, respectively, and the isotope 13 could be a back-scatter source in which Am-241 is used for exciting back-scatter radiation from a copper or other metal target. In another such alternative embodiment, the isotopes 13 and 14 could both be Am-241, where the detectors 17 and 18 are sensitive to different energy levels emitted by Am-241 (i.e., a gamma radiation energy band and an X-ray radiation energy band).

The present invention has been described above in terms of particular isotopes that are especially useful for measuring weight percentages of particular constituents of a particular composite material. However, other isotopes that would be more suitable for measuring weight percentages of the constituents of other materials would be apparent to practioners in the art upon perusing the foregoing specification and the accompanying drawing. Accordingly, the foregoing description is to be understood as being merely illustrative of the invention. The invention is more generally defined by the following claims and their equivalents.

I claim:

1. A method for determining weight percentages of first and second constituents of a solid composite material, said first constituent being graphite fibers distributed through said second constituent, each of said first and second constituents having a characteristic energy-dependent radiation absorption coefficient for ionizing radiation, said method comprising the steps of:
   (a) identifying said first and second constituents in terms of chemical formulation;
   (b) selecting a plurality of distinct energy bands of ionizing radiation, the radiation absorption coefficients of said first and second constituents for said ionizing radiation having ratios with respect to each other that are different for each of said distinct energy bands;
   (c) exposing a common surface area of a sample of said composite material to said ionizing radiation in each of said distinct energy bands;
   (d) measuring the energy that is transmitted through said sample in each of said distinct energy bands when said surface area of said sample is exposed to said ionizing radiation in each of said distinct energy bands; and
   (e) calculating a weight percentage for each of said first and second constituents of said composite material from an algorithm whose variables include:
      (i) volume density of each of said first and second constituents;
      (ii) thickness of said sample through which said energy in each of said distinct energy bands is transmitted;
      (iii) mass absorption cross section for each of said first and second constituents; and
      (iv) a corresponding ratio for each of said distinct energy bands of ionizing radiation, each of said ratios being a ratio of the energy that would be measured in a particular one of said energy bands if said sample were not present in said ionizing radiation to the energy in said particular one of said energy bands that is transmitted through said sample when said surface area of said sample is exposed to said ionizing radiation.

2. The method of claim 1 wherein said radiation in said selected energy bands is provided by a plurality of radioactive isotopes.

3. The method of claim 2 wherein said radiation is provided by three different sources, each source comprising a different isotope, namely, Cd-109 isotope, Fe-55 isotope and Am-241 isotopes.

4. The method of claim 2 wherein said radiation is provided by three different sources, one of said sources comprising Cd-109 isotope, and two of said sources comprising Am-241 isotope, one of said Am-241 sources being used to excite back-scatter radiation from a target.

5. The method of claim 4 wherein said target comprises copper.

6. The method of claim 2 wherein said radiation is provided by two different sources, one of said sources comprising Cd-109 isotope and the other of said sources comprising Am-241 isotope, and wherein said Am-241 isotope provides said radiation in two distinct energy bands.

7. The method of claim 1 wherein said common surface area of said sample is exposed to said ionizing radiation in said plurality of distinct energy bands simultaneously, and wherein said energy that is transmitted through said sample in each of said energy bands is measured separately but simultaneously with the energy that is transmitted through said sample in the others of said energy bands.

8. An apparatus for determining weight percentages of first and second constituents of a solid composite material, said first constituent being graphite fibers distributed through said second constituent, each of said first and second constituents having a characteristic energy-dependent radiation absorption coefficient for ionizing radiation, said apparatus comprising:
   (a) a plurality of sources of ionizing radiation, each of said sources emitting ionizing radiation in a characteristically different energy band, the radiation absorption coefficients of said first and second constituents for said ionizing radiation having ratios with respect to each other that are different for each of said energy bands;
   (b) means for exposing a common surface area of a sample of said composite material to ionizing radiation from each of said sources;
   (c) means for measuring the energy transmitted from corresponding ones of said ionizing radiation sources through said sample, and for generating electrical signals indicative of the energy transmitted through said sample in each of said energy bands when said surface area of said sample is exposed to said ionizing radiation from each of said sources, said means for measuring said energy and for generating said electrical signals comprising a plurality of detectors, each one of said detectors being disposed to detect the energy in a particular energy band transmitted through said sample from a corresponding particular one of said ionizing radiation sources; and
   (d) means for analyzing said electrical signals, and for generating therefrom the weight percentages of said first and second constituents of said composite material.

9. The apparatus of claim 8 comprising three different sources of radiation, each of said sources comprising a different isotope, namely, Cd-109 isotope, Fe-55 isotope and Am-241 isotope.

10. The apparatus of claim 8 comprising three different sources of radiation, one of said sources being Cd-109 isotope, and two of said sources being Am-241 isotope, one of said Am-241 sources being used to excite back-scatter radiation from a target.

11. The apparatus of claim 10 wherein said target comprises copper.

12. The apparatus of claim 8 comprising two different sources of radiation, one of said sources being Cd-109 isotope and the other of said sources being Am-241 isotope, said Am-241 isotope providing gamma radiation in one energy band and X-ray radiation in another energy band.

13. The apparatus of claim 8 wherein said means for exposing said common surface area of said sample to said ionizing radiation exposes said surface area to ionizing radiation in each of said different energy bands simultaneously, and wherein said detectors are disposed to detect the energy transmitted through said sample in said different energy bands simultaneously.

14. A method for determining weight percentages of three different constituents of a solid composite material, said first constituent being graphite fibers distributed through said second constituent, each of said constituents having a characteristically different energy-dependent radiation absorption coefficient for ionizing radiation, said method comprising:
   (a) identifying each of said constituents of said composite material by chemical formulation;
   (b) selecting three distinct energy bands of ionizing radiation, the different radiation absorption coefficients of said constituents for said ionizing radiation having ratios with respect to each other that are different for each of said distinct energy bands;
   (c) exposing a common surface area of said sample of said composite material to said ionizing radiation in each of said distinct energy bands;
   (d) measuring the energy that is transmitted through said sample in each of said three distinct energy bands when said surface area of said sample is exposed to said ionizing radiaion in each of said three distinct energy bands; and
   (e) calculating a weight percentage for each of said three constituents of said composite material from an algorithm whose variables include:
      (i) volume density of each of said three constituents;
      (ii) thickness of said sample through which said energy in each of said three distinct energy bands is transmitted;
      (iii) mass absorption cross section for each of said three constituents; and
      (iv) three ratios corresponding to said three distinct energy bands of ionizing radiation, each of said ratios being a ratio of the energy that would be measured in a particular one of said energy bands if said sample were not present in said ionizing radiation to the energy in said particular one of said energy bands that is transmitted through said sample when said surface area of said sample is exposed to said ionizing radiation.

15. The method of claim 14 wherein said radiation is provided by a plurality of radioactive isotopes.

16. The method of claim 15 wherein said radiation is provided by three different sources, each source comprising a different isotope, namely, Cd-109 isotope, Fe-55 isotope and Am-241 isotope.

17. The method of claim 15 wherein said radiation is provided by three different sources, one of said sources comprising Cd-109 isotope, and two of said sources comprising Am-241 isotope, one of said Am-241 sources being used to excite back-scatter radiation from a target.

18. The method of claim 17 wherein said target comprises copper.

19. The method of claim 15 wherein said radiation is provided by two different sources, one of said sources comprising Cd-109 isotope and the other of said sources comprising Am-241 isotope, said Am-241 isotope providing gamma radiation in one energy band and X-ray radiation in another energy band.

20. The method of claim 14 wherein said common surface area of said sample is exposed to said ionizing radiation in said three distinct energy bands simultaneously, and wherein said energy that is transmitted through said sample in each of said three energy bands is measured separately but simultaneously with the energy that is transmitted through said sample in the other two of said three energy bands.

21. The method of claim 14 wherein said algorithm has the form $$\alpha_1 = \frac{\frac{1}{\rho_1 t} \begin{vmatrix} \ln(N_0/N)_{E_1} & (\mu/\rho)_{21} & (\mu/\rho)_{31} \\ \ln(N_0/N)_{E_2} & (\mu/\rho)_{22} & (\mu/\rho)_{32} \\ \ln(N_0/N)_{E_3} & (\mu/\rho)_{23} & (\mu/\rho)_{33} \end{vmatrix}}{\begin{vmatrix} (\mu/\rho)_{11} & (\mu/\rho)_{21} & (\mu/\rho)_{31} \\ (\mu/\rho)_{12} & (\mu/\rho)_{22} & (\mu/\rho)_{32} \\ (\mu/\rho)_{13} & (\mu/\rho)_{23} & (\mu/\rho)_{33} \end{vmatrix}},$$

$$\alpha_2 = \frac{\frac{1}{\rho_2 t} \begin{vmatrix} (\mu/\rho)_{11} & \ln(N_0/N)_{E_1} & (\mu/\rho)_{31} \\ (\mu/\rho)_{12} & \ln(N_0/N)_{E_2} & (\mu/\rho)_{32} \\ (\mu/\rho)_{13} & \ln(N_0/N)_{E_3} & (\mu/\rho)_{33} \end{vmatrix}}{\begin{vmatrix} (\mu/\rho)_{11} & (\mu/\rho)_{21} & (\mu/\rho)_{31} \\ (\mu/\rho)_{12} & (\mu/\rho)_{22} & (\mu/\rho)_{32} \\ (\mu/\rho)_{13} & (\mu/\rho)_{23} & (\mu/\rho)_{33} \end{vmatrix}},$$

and $$\alpha_3 = \frac{\frac{1}{\rho_3 t} \begin{vmatrix} (\mu/\rho)_{11} & (\mu/\rho)_{21} & \ln(N_0/N)_{E_1} \\ (\mu/\rho)_{12} & (\mu/\rho)_{22} & \ln(N_0/N)_{E_2} \\ (\mu/\rho)_{13} & (\mu/\rho)_{23} & \ln(N_0/N)_{E_3} \end{vmatrix}}{\begin{vmatrix} (\mu/\rho)_{11} & (\mu/\rho)_{21} & (\mu/\rho)_{31} \\ (\mu/\rho)_{12} & (\mu/\rho)_{22} & (\mu/\rho)_{32} \\ (\mu/\rho)_{13} & (\mu/\rho)_{23} & (\mu/\rho)_{33} \end{vmatrix}},$$

where $\alpha$, $\alpha_2$ and $\alpha_3$ represent, respectively, the fractional weight percentages of said three different constituents of said composite material; $\rho_1$, $\rho_2$ and $\rho_3$ represent, respectively, the volume densities of said three different constituents; $t$ represents the thickness of said sample; $E_1$, $E_2$ and $E_3$ represent said three distinct energy bands; $N_0$ represents the amount of energy that would be detected if said sample were not present in said radiation, and N represents the amount of energy that is transmitted through said sample when said sample is exposed to said radiation; and $(\mu/\rho)_{ij}$ represents the mass absorption cross section of the ith constituent (where i=1, 2, 3) for the jth energy band (where j=1, 2, 3).

* * * * *